(12) United States Patent
De Boer et al.

(10) Patent No.: US 7,259,123 B2
(45) Date of Patent: Aug. 21, 2007

(54) CATALYTIC TRIMERIZATION AND TETRAMERIZATION OF OLEFINIC MONOMERS

(75) Inventors: Eric Johannes Maria De Boer, Amsterdam (NL); Harry Van Der Heijden, Amsterdam (NL); Quoc An On, Amsterdam (NL); Johan Paul Smit, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/398,777

(22) Filed: Apr. 6, 2006

(65) Prior Publication Data

US 2006/0235250 A1 Oct. 19, 2006

(30) Foreign Application Priority Data

Apr. 8, 2005 (EP) .................. 05252220

(51) Int. Cl.
*B01J 31/00* (2006.01)
*C07C 2/08* (2006.01)

(52) U.S. Cl. .................. 502/162; 502/103; 502/113; 502/117; 502/167; 585/510; 585/513

(58) Field of Classification Search .............. 502/103, 502/117, 162, 167, 113; 585/510, 513
See application file for complete search history.

(56) References Cited

U.S. PATENT DOCUMENTS

| 5,198,563 | A | 3/1993 | Reagen et al. | 556/57 |
|---|---|---|---|---|
| 5,523,507 | A | 6/1996 | Reagen et al. | 585/513 |
| 5,968,866 | A | 10/1999 | Wu | 502/155 |
| 6,800,702 | B2 * | 10/2004 | Wass | 526/124.3 |
| 2003/0166456 | A1 | 9/2003 | Wass | 502/102 |
| 2005/0113622 | A1 | 5/2005 | Drent et al. | 585/521 |

FOREIGN PATENT DOCUMENTS

| WO | 2002/04119 | 7/2004 |
|---|---|---|
| WO | 2004/056478 | 7/2004 |
| WO | 2004/056479 | 7/2004 |
| WO | 2004/056480 | 7/2004 |
| WO | WO 2004/056479 | * 7/2004 |
| WO | 2005/039758 | 5/2005 |
| WO | WO2005123633 | 12/2005 |

OTHER PUBLICATIONS

Chem. Commun., 2002, 8, "High activity ethylene trimerisation catalyst based on diphosphine ligands" pp. 858-859.
Burgess et al., Stereochemically Matched (and Mismatched) Bisphosphine Ligands: DIP-DIRAMP Hybrids Organometallics, vol. 11, 1992, pp. 3588-3600, p. 3591 Figure 3, compounds 6, 7, 9.

* cited by examiner

*Primary Examiner*—Caixia Lu
(74) *Attorney, Agent, or Firm*—Donald F. Haas

(57) ABSTRACT

A catalyst precursor composition comprising a) a source of chromium, molybdenum or tungsten; b) a first ligand having the general formula (I);

$$(R^1)(R^2)P-X-P(R^3)(R^4) \qquad (I)$$

wherein X is a bivalent organic bridging group; $R^1$ and $R^3$ are independently selected from, hydrocarbyl, substituted hydrocarbyl, heterohydrocarbyl and substituted heterohydrocarbyl groups, with the proviso that when $R^1$ and $R^3$ are aromatic groups they do not contain a polar substituent at any of the ortho-positions; $R^2$ and $R^4$ are independently selected from optionally substituted aromatic groups, each $R^2$ and $R^4$ bearing a polar substituent on at least one of the ortho-positions; and c) a second ligand having the general formula (II);

$$(R^{1'})(R^{2'})P-X'-P(R^{3'})(R^{4'}) \qquad (II)$$

wherein X' is a bridging group of the formula —N($R^{5'}$)—, wherein $R^{5'}$ is selected from hydrogen, a hydrocarbyl group, a substituted hydrocarbyl group, a heterohydrocarbyl group, a substituted heterohydrocarbyl group, a silyl group or derivative thereof; and $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups of which at least one of $R^{1'}$, $R^{2'}$, $R^{3'}$ and $R^{4'}$ is substituted with a polar substituent, or $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups, wherein any substituents on one or more of $R^{1'}$, $R^{2'}$, $R^{3'}$ and $R^{4'}$ are non-polar. The present invention also relates to a catalyst system comprising the catalyst precursor composition of the present invention and a cocatalyst.

12 Claims, No Drawings

CATALYTIC TRIMERIZATION AND TETRAMERIZATION OF OLEFINIC MONOMERS

FIELD OF THE INVENTION

The present invention relates to a catalyst system for the oligomerization of olefinic monomers. The present invention also relates to a process for the oligomerization of olefinic monomers.

BACKGROUND OF THE INVENTION

The efficient catalytic trimerization and tetramerization of olefinic monomers, such as the trimerization and tetramerization of ethylene to 1-hexene and 1-octene, is an area of great interest for the production of olefinic trimers and tetramers of varying degrees of commercial value. In particular, 1-hexene is a valuable comonomer for linear low-density polyethylene (LLDPE) and 1-octene is valuable as a chemical intermediate in the production of plasticizer alcohols, fatty acids, detergent alcohol and lubrication oil additives as well as a valuable comonomer in the production of polymers such as polyethylene. 1-Hexene and 1-octene can be produced by a conventional transition metal oligomerization process, although the trimerization and tetramerization routes are preferred.

Several different catalytic systems have been disclosed in the art for the trimerization of ethylene to 1-hexene. A number of these catalysts are based on chromium.

Chem. Commun., 2002, 8, 858-859 (BP), discloses chromium complexes of ligands of the type $Ar_2PN(Me)PAr_2$ (Ar=ortho-methoxy-substituted aryl group) as catalysts for the trimerization of ethylene. U.S. Pat. No. 6,800,702 (BP) discloses a catalyst for the trimerization of olefins comprising a source of chromium, molybdenum or tungsten, a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally an activator. The ligand used in most of the examples is (2-methoxyphenyl)$_2$PN(Me)P(2-methoxyphenyl)$_2$.

Although the catalysts disclosed in the BP documents mentioned above have good selectivity for 1-hexene within the $C_6$ fraction, a relatively high level of by-product formation (e.g. $C_{10}$ by-products) is observed.

Catalytic systems for the tetramerization of ethylene to 1-octene have recently been developed. A number of these catalysts are based on chromium.

WO 2004/056478 and WO 2004/056479 (Sasol) disclose catalyst compositions and processes for the tetramerization of olefins. The catalyst compositions disclosed in WO 2004/056478 comprise a transition metal and a heteroatomic ligand having the general formula $(R)_nA—B—C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m is determined by the respective valence and oxidation state of A and C. The catalyst compositions disclosed in WO 2004/056479 comprise a transition metal and a heteroatomic ligand having the general formula $(R)_nA—B—C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group and n and m is determined by the respective valence and oxidation state of A and/or C.

WO 2004/056480 (Sasol) discloses the tandem tetramerization and polymerisation of ethylene. Specifically, WO 2004/056480 discloses a process for polymerising olefins to produce branched polyolefins in the presence of a distinct polymerization catalyst and a distinct tetramerization catalyst, wherein the tetramerization catalyst produces 1-octene in a selectivity greater than 30% and the 1-octene produced is at least partially incorporated into the polyolefin chain.

Although the tetramerization catalysts disclosed in the Sasol documents mentioned above have good selectivity for 1-octene within the $C_8$ fraction, again, a relatively high level of by-product formation is observed. Typically, the by-product consists of $C_6$ compositions; however, only about 70 to 80% wt. of the $C_6$ by-product composition is 1-hexene, with the remaining $C_6$ by-product comprising compounds such as methylcyclopentane and methylenecyclopentane. The presence of these remaining $C_6$ by-product compositions, which have very little commercial use or value, is highly undesirable from both an economic point of view as well as from a product separation point of view.

It has now been surprisingly found that the catalyst system and process of the present invention provide an efficient route for the selective production of 1-hexene and 1-octene from ethylene while reducing the level of by-product formation, especially $C_{10}$ by-products, solids (i.e. heavy waxes and/or polyethylene) and $C_6$ compositions/isomers other than 1-hexene.

SUMMARY OF THE INVENTION

The present invention provides a catalyst precursor composition comprising:

a) a source of chromium, molybdenum or tungsten;

b) a first ligand having the general formula (I);

wherein:

X is a bivalent organic bridging group;

$R^1$ and $R^3$ are independently selected from hydrocarbyl, substituted hydrocarbyl, heterohydrocarbyl and substituted heterohydrocarbyl groups, with the proviso that when $R^1$ and $R^3$ are aromatic groups they do not contain a polar substituent at any of the ortho-positions;

$R^2$ and $R^4$ are independently selected from optionally substituted aromatic groups, each $R^2$ and $R^4$ bearing a polar substituent on at least one of the ortho-positions;

c) a second ligand having the general formula (II);

wherein:

X' is a bridging group of the formula $—N(R^{5'})—$, wherein $R^{5'}$ is selected from hydrogen, a hydrocarbyl group, a substituted hydrocarbyl group, a heterohydrocarbyl group, a substituted heterohydrocarbyl group, a silyl group or derivative thereof; and $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups of which at least one of $R^{1'}$, $R^{2'}$, $R^{3'}$ and $R^{4'}$ is substituted with a polar substituent, or $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups, wherein any substituents on one or more of $R^{1'}$, $R^{2'}$, $R^{3'}$ and $R^{4'}$ are non-polar.

In another embodiment, the present invention provides a catalyst system comprising the catalyst precursor composition of the present invention and a cocatalyst.

The present invention also provides a process for the trimerization and tetramerization of olefinic monomers, particularly the trimerization and tetramerization of ethylene to 1-hexene and 1-octene, wherein the process comprises contacting at least one olefinic monomer with the catalyst system of the present invention under trimerization and tetramerization reaction conditions.

The present invention further relates to the use of the catalysts system of the present invention for the trimerization and tetramerization of olefinic monomers, especially for the trimerization and tetramerization of ethylene to 1-hexene and 1-octene.

The present invention also provides an olefinic product composition which comprises a combined total content of 1-hexene and 1-octene in the range of from 88 to 98% wt of the overall product composition, preferably from 90 to 98% wt and more preferably from 92 to 98% wt, wherein the 1-hexene content is at least 15% wt, more preferably at least 20% wt and most preferably at least 25% wt, of the overall product composition and the 1-octene content is at least 15% wt, more preferably at least 20% wt and most preferably at least 25% wt, of the overall product composition.

DETAILED DESCRIPTION OF THE INVENTION

As used herein, the term "trimerization" means the catalytic trimerization of an olefinic monomer to give a product composition enriched in the compound derived from the reaction of three of said olefinic monomers. The term trimerization includes the cases wherein all the olefinic monomers in the feed stream are identical as well as the cases wherein the feed stream contains two or more different olefinic monomers.

In particularly, the term "trimerization" when used in relation to the trimerization of ethylene means the trimerization of ethylene to form a $C_6$ alkene, especially 1-hexene.

The term "trimerization selectivity" when used in relation to the trimerization of ethylene to 1-hexene means the amount of $C_6$ fraction formed within the product composition.

The term "1-hexene selectivity" when used in relation to the trimerization of ethylene to 1-hexene means the amount of 1-hexene formed within the $C_6$ fraction of the product composition. The overall yield of 1-hexene in the trimerization of ethylene is the product of the "trimerization selectivity" multiplied by the "1-hexene selectivity".

The term "tetramerization" means the catalytic tetramerization of an olefinic monomer to give a product composition enriched in the compound derived from the reaction of four of said olefinic monomers. The term tetramerization includes the cases wherein all the olefinic monomers in the feed stream are identical as well as the cases wherein the feed stream contains two or more different olefinic monomers.

In particularly, the term "tetramerization" when used in relation to the tetramerization of ethylene means the tetramerization of ethylene to form a $C_8$ alkene, especially 1-octene.

The term "tetramerization selectivity" when used in relation to the tetramerization of ethylene to 1-octene means the amount of $C_8$ fraction formed within the product composition.

The term "1-octene selectivity" when used in relation to the tetramerization of ethylene to 1-octene means the amount of 1-octene formed within the $C_8$ fraction of the product composition. The overall yield of 1-octene in the tetramerization of ethylene is the product of the "tetramerization selectivity" multiplied by the "1-octene selectivity".

In one embodiment of the present invention, the catalyst precursor composition system comprises:
  a) a source of chromium, molybdenum or tungsten;
  b) the first ligand; and
  c) the second ligand;

In another embodiment of the present invention, the catalyst system comprises:
  a) a source of chromium, molybdenum or tungsten;
  b) the first ligand;
  c) the second ligand; and
  d) a cocatalyst.

Each of these four catalyst components is described in detail below.

The source of chromium, molybdenum or tungsten, component (a), for the catalyst system can include simple inorganic and organic salts of chromium, molybdenum or tungsten. Examples of simple inorganic and organic salts are halides, acetylacetonates, carboxylates, oxides, nitrates, sulfates and the like. Further sources of chromium, molybdenum or tungsten can also include co-ordination and organometallic complexes, for example chromium trichloride tris-tetrahydrofuran complex, (benzene)tricarbonylchromium, chromium hexacarbonyl, and the like. Preferably, the source of chromium, molybdenum or tungsten, component (a), is an organic salt of chromium, molybdenum or tungsten.

In one embodiment of the present invention, the source of chromium, molybdenum or tungsten, component (a), is a simple inorganic or organic salt of chromium, molybdenum or tungsten, preferably an organic salt, which is soluble in a solvent such as those disclosed in U.S. Pat. No. 6,800,702, which is herein incorporated by reference.

The source of chromium, molybdenum or tungsten can also include a mixture of any combination of simple inorganic salts, simple organic salts, co-ordination complexes and organometallic complexes.

In a preferred embodiment herein, component (a) is a source of chromium, particularly chromium (III).

Preferred sources of chromium for use herein are simple inorganic and organic salts of chromium and co-ordination or organometallic complexes of chromium. More preferred sources of chromium for use herein are the organic salts of chromium, such as salts of carboxylic acids, preferably salts of alkanoic acids containing 1 to 30 carbon atoms, salts of aliphatic-β-diketones and salts of β-ketoesters (e.g. chromium (III) 2-ethylhexanoate, chromium (III) octanoate and chromium (III) acetylacetonate), and halide salts of chromium, such as chromium trichloride, chromium trichloride tris-tetrahydrofuran complex, chromium tribromide, chromium trifluoride, and chromium tri-iodide. A particularly preferred source of chromium for use herein is chromium (III) acetylacetonate, also called chromium tris(2,4-pentanedionate), $Cr(acac)_3$.

The first ligand of the catalyst system of the present invention, component (b), is of the general formula (I);

$(R^1)(R^2)P-X-P(R^3)(R^4)$     (I)

wherein:

X is a bivalent organic bridging group which may comprise from 1 to 10 carbon atoms in the bridge;

$R^1$ and $R^3$ are independently selected from hydrocarbyl, substituted hydrocarbyl, heterohydrocarbyl and substituted heterohydrocarbyl groups with the proviso that when $R^1$ and $R^3$ are aromatic groups they do not contain a polar substituent at any of the ortho-positions;

$R^2$ and $R^4$ are independently selected from optionally substituted aromatic groups, each $R^2$ and $R^4$ bearing a polar substituent on at least one of the ortho-positions.

In the general formula (I), X represents a bivalent organic bridging group, which may comprise from 1 to 10, preferably from 2 to 6, more preferably from 2 to 4 and especially from 2 to 3 carbon atoms in the bridge. In a preferred embodiment there may be 2 carbon atoms in the bridge.

By "in the bridge" is understood to be the shortest connection between the two phosphorus atoms.

Suitable bridging groups include substituted and unsubstituted alkylene groups. The alkylene groups can optionally contain one or more heteroatoms in the bridge, such as N (e.g. —N(Me)-), S (e.g. —SO$_2$—), Si or O. Preferably, the alkylene group contains only carbon atoms in the bridge.

The alkylene groups can be substituted with one or more substituents. The substituents can be attached to any part of the bridging group.

The substituents on the alkylene bridging group can contain carbon atoms and/or heteroatoms. Suitable substituents include hydrocarbyl groups which may be straight-chain or branched, saturated or unsaturated, aromatic or non-aromatic. The hydrocarbyl substituents may optionally contain heteroatoms such as Si, S, N or O. Suitable aromatic hydrocarbyl substituents include monocyclic and polycyclic aromatic groups, preferably having from 5 to 10 carbon atoms in the ring, such as phenyl and $C_1$-$C_4$ alkyl phenyl groups. Suitable non-aromatic hydrocarbyl substituents include linear or branched alkyl or cycloalkyl groups, preferably having from 1 to 10 carbon atoms, more preferably 1 to 4 carbon atoms.

Other suitable substituents of the alkylene bridging group include halides such as chloride, bromide and iodide, thiol, —OH, $A^1$—O—, —S-$A^1$, —CO-$A^1$, —NH$_2$, —NHA$^1$, —NA$^1$A$^2$, —CO—NA$^1$A$^2$, —NO$_2$, =O, in which $A^1$ and $A^2$, independently, are non-aromatic groups preferably having from 1 to 10 carbon atoms, more preferably 1 to 4 carbon atoms, e.g. methyl, ethyl, propyl and isopropyl.

When the alkylene bridging group is substituted, preferred substituents are hydrocarbyl groups. Particularly preferred hydrocarbyl substituents are $C_1$-$C_4$ alkyl groups, preferably methyl, ethyl, propyl, isopropyl, butyl, isobutyl, most preferably methyl.

Examples of non-substituted alkylene bridging groups include methylene, ethylene and trimethylene groups. Examples of substituted alkylene bridging groups include 2,2-dimethyl-trimethylene, 2,2-diethyl-trimethylene, 2,2-dimethyl-tetramethylene, 2-methyl-trimethylene, 2-hydroxymethyl-trimethylene and 2,2-di-hydroxymethyl-trimethylene.

Particularly preferred organic bridging groups for use herein are unsubstituted alkylene bridging groups. An especially preferred organic bridging group is ethylene, that is, —CH$_2$—CH$_2$—.

Other suitable bridging groups are those where the bridge forms part of a non-aromatic or aromatic ring structure. Such bridging groups comprise one or more substituted or unsubstituted, saturated or unsaturated non-aromatic ring structures and/or one or more substituted or unsubstituted aromatic (including heteroaromatic) ring structures. The non-aromatic ring structure may be interrupted by one or more heteroatoms such as N, S, Si or O. Preferably such a bridging group still contains only 2 to 6 carbon atoms in the bridge.

Suitable non-aromatic ring structures include cyclopentane, cyclohexane, cyclohexene, cyclopentene, 3,4-furan and 3,4-thiophene.

Suitable aromatic ring structures include phenylene, in particular 1,2-phenylene, and naphthylene, in particular 1,8- or 1,2-naphthylenes.

The ring structures may be substituted with any kind of substituent, including heteroatoms, alkyl groups, cycloalkyl groups and aromatic groups. Suitable substituents include those mentioned above in relation to alkylene bridging groups. It is preferred that the two phosphorus atoms are attached to the ring system at adjacent positions, i.e. relative positions 1 and 2 in the ring.

$R^1$ and $R^3$ are independently selected from, hydrocarbyl, substituted hydrocarbyl, heterohydrocarbyl and substituted heterohydrocarbyl groups, with the proviso that when $R^1$ and $R^3$ are aromatic groups they do not contain a polar substituent at any of the ortho-positions.

The term "hydrocarbyl" as used herein refers to a group only containing carbon and hydrogen atoms. The hydrocarbyl group may be a saturated or unsaturated, linear or branched alkyl, a non-aromatic ring or an aromatic ring. Preferred hydrocarbyl groups for use herein are those containing from 1 to 20 carbon atoms.

The term "substituted hydrocarbyl" as used herein refers to hydrocarbyl groups which contain one or more inert heteroatom containing functional groups. By "inert heteroatom containing functional groups" is meant that the functional groups do not interfere to any substantial degree with the trimerization and tetramerization process.

The term "heterohydrocarbyl" as used herein refers to a hydrocarbyl group wherein one or more of the carbon atoms is replaced by a heteroatom, such as S, N or O. The term "substituted heterohydrocarbyl" as used herein refers to heterohydrocarbyl groups which contain one or more inert heteroatom containing functional groups.

The term "aromatic" as used herein, refers to a monocyclic or polycyclic, aromatic or heteroaromatic ring which may have from 5 to 14 ring atoms, and optionally may have from 1 to 3 heteroatoms selected from N, O and S. Preferably, the aromatic groups are monocyclic or polycyclic aromatic rings, such as cyclopentadienyl, phenyl, naphthyl or anthracenyl. Even more preferred aromatic groups are monocyclic or polycyclic aromatic rings having from 5 to 10 ring atoms. Especially preferred aromatic groups are monocyclic aromatic rings containing from 5 to 6 carbon atoms, such as phenyl and cyclopentadienyl, and a most preferred aromatic group is a phenyl group.

The term "substituted aromatic" as used herein means that the aromatic group may be substituted with one or more substituents. Suitable substituents include those mentioned above in relation to the alkylene bridging group.

In one preferred embodiment, $R^1$ and $R^3$ are independently selected from substituted or unsubstituted aromatic groups which do not contain a polar substituent at any of the ortho-positions. By the term "ortho-position" when used in relation to substituents on the aromatic $R^1$, $R^2$, $R^3$ and $R^4$ groups, it is meant that the substituent is in the ortho position relative to the atom bonded to the phosphorus atom. In an even more preferred embodiment, $R^1$ and $R^3$ are independently selected from optionally substituted phenyl groups which do not contain a polar substituent at any of the ortho-positions. In a most preferred embodiment, $R^1$ and $R^3$ are independently selected from optionally substituted phenyl groups which do not contain any polar substituents. In an especially preferred embodiment, $R^1$ and $R^3$ are unsubstituted phenyl groups.

It is preferred that the $R^1$ and $R^3$ groups are the same.

$R^2$ and $R^4$ are independently selected from optionally substituted aromatic groups, each $R^2$ and $R^4$ group bearing a polar substituent on at least one of the ortho-positions. For the avoidance of doubt, the phrase "each $R^2$ and $R^4$ bearing a polar substituent on at least one of the ortho-positions" means that, in the same ligand, $R^2$ is substituted with a polar substituent on one or both of its ortho positions and $R^4$ is substituted with a polar substituent on one or both of its ortho-positions.

The term "optionally substituted" in relation to $R^2$ and $R^4$ means that, in addition to the polar substituent on at least one of the ortho-positions, the $R^2$ and $R^4$ groups may contain one or more substituents. Suitable substituents include those mentioned in relation to the alkylene bridging group.

Preferably, $R^2$ and $R^4$ are independently selected from optionally substituted aromatic groups which may have from 5 to 14 ring atoms, preferably from 5 to 10 ring atoms, wherein each $R^2$ and $R^4$ bears a polar substituent on at least one of the ortho-positions.

In one preferred embodiment, $R^2$ and $R^4$ are independently selected from optionally substituted phenyl groups, wherein each $R^2$ and $R^4$ bears a polar substituent on at least one of the ortho-positions.

Preferably, each of $R^2$ and $R^4$ bears a polar substituent on one of the two ortho-positions.

Polar is defined by IUPAC as an entity with a permanent electric dipole moment. Therefore, as used herein, the term "polar substituents" means a substituent which incorporates a permanent electric dipole moment.

Suitable polar substituents for use herein may include but are not necessarily limited to, optionally branched $C_1$-$C_{20}$ alkoxy groups, i.e. hydrocarbyl groups connected to the $R^2$ and $R^4$ aromatic ring, or $R^1$ and $R^3$ provided that when they are selected from substituted or unsubstituted aromatic groups the polar substituent is not attached to any of the ortho-positions, through an oxygen bridging atom; optionally substituted $C_5$-$C_{14}$ aryloxy groups, i.e. optionally substituted aromatic groups connected to the $R^2$ and $R^4$ aromatic ring, or $R^1$ and $R^3$ provided that when they are selected from substituted or unsubstituted aromatic groups the polar substituent is not attached to any of the ortho-positions, through an oxygen bridging atom; optionally branched $C_1$-$C_{20}$ alkoxy($C_1$-$C_{20}$)alkyl groups, i.e. $C_1$-$C_{20}$ hydrocarbyl groups bearing a $C_1$-$C_{20}$ alkoxy group; hydroxyl; amino; (di-)$C_1$-$C_6$ alkylamino; nitro; $C_1$-$C_6$ alkylsulphonyl; $C_1$-$C_6$ alkylthio ($C_1$-$C_6$)alkyl groups; sulphate; heterocyclic groups, especially with at least one N and/or O ring atom; and tosyl groups.

Examples of suitable polar substituents may include methoxy, ethoxy, isopropoxy, phenoxy, pentafluorophenoxy, trimethylsiloxy, dimethylamino, methylsulphonyl, tosyl, methoxymethyl, methylthiomethyl, 1,3-oxazolyl, hydroxyl, amino, nitro and the like.

Preferably, the polar substituents on $R^2$ and $R^4$ may be independently selected from optionally branched $C_1$-$C_{20}$ alkoxy groups, optionally substituted $C_5$-$C_{14}$ aryloxy groups, and optionally branched $C_1$-$C_{20}$ alkyl($C_1$-$C_{20}$) alkoxy groups. More preferably, the polar substituents on $R^2$ and $R^4$ may be independently selected from optionally branched $C_1$-$C_{20}$ alkoxy groups, especially optionally branched $C_1$-$C_6$ alkoxy groups such as, for example, methoxy, ethoxy or isopropoxy. A particularly preferred polar substituent on $R^2$ and $R^4$ is methoxy.

It is preferred that the $R^2$ and $R^4$ groups are the same and bear the same number and type of polar substituent(s). It is particularly preferred that $R^2$ bears only one polar substituent on one of its two ortho-positions and that $R^4$ bears only one polar substituent on one of its two ortho-positions.

The ligands according to formula (I) may be prepared using procedures known to one skilled in the art or disclosed in published literature. Examples of such compounds are:
(2-methoxyphenyl)(phenyl)PCH$_2$CH$_2$P(2-methoxyphenyl)(phenyl)
(2-methoxyphenyl)(phenyl)PCH$_2$P(2-methoxyphenyl)(phenyl)
(2-methoxyphenyl)(phenyl)PCH$_2$CH$_2$CH$_2$P(2-methoxyphenyl)(phenyl)
(2-ethoxyphenyl)(phenyl)PCH$_2$CH$_2$P(2-ethoxyphenyl)(phenyl)
(2-ethoxyphenyl)(phenyl)PCH$_2$P(2-ethoxyphenyl)(phenyl)
(2-ethoxyphenyl)(phenyl)PCH$_2$CH$_2$CH$_2$P(2-ethoxyphenyl)(phenyl)
(2-isopropoxyphenyl)(phenyl)PCH$_2$CH$_2$P(2-isopropoxyphenyl)(phenyl)
(2-isopropoxyphenyl)(phenyl)PCH$_2$P(2-isopropoxyphenyl)(phenyl)
(2-isopropoxyphenyl)(phenyl)PCH$_2$CH$_2$CH$_2$P(2-isopropoxyphenyl)(phenyl)

A particularly preferred ligand for use herein is (2-methoxyphenyl)(phenyl)PCH$_2$CH$_2$P(2-methoxyphenyl)(phenyl).

The second ligand of the catalyst system of the present invention, component (c), is of the general formula (II);

$$(R^{1'})(R^{2'})P-X'-P(R^{3'})(R^{4'}) \qquad (II)$$

wherein:

X' is a bridging group of the formula —N($R^{5'}$)—, wherein $R^{5'}$ is selected from hydrogen, a hydrocarbyl group, a substituted hydrocarbyl group, a heterohydrocarbyl group, a substituted heterohydrocarbyl group, a silyl group or derivative thereof; and $R^{1'}$, $R^{2'}$, $R^{3'}$ and $R^{4'}$ are, in a first embodiment, independently selected from hydrocarbyl, substituted hydrocarbyl, heterohydrocarbyl and substituted heterohydrocarbyl groups of which at least one of $R^{1'}$, $R^{2'}$, $R^{3'}$ and $R^{4'}$ is substituted with a polar substituent, or $R^{1'}$, $R^{2'}$, $R^{3'}$ and $R^{4'}$ are, in a second embodiment, independently selected from hydrocarbyl, substituted hydrocarbyl, heterohydrocarbyl and substituted heterohydrocarbyl groups, wherein any substituents on one or more of $R^{1'}$, $R^{2'}$, $R^{3'}$ and $R^{4'}$ are non-polar.

The bridging group X' is of the formula —N($R^{5'}$)—, wherein $R^{5'}$ is preferably hydrogen, a hydrocarbyl group, a substituted hydrocarbyl group, a heterohydrocarbyl group, a substituted heterohydrocarbyl group, a silyl group or derivative thereof. Typically, $R^{5'}$ may be selected from hydrogen or the groups consisting of alkyl, substituted alkyl, aryl, substituted aryl, aryloxy, substituted aryloxy, alkenyl, substituted alkenyl, cycloalkyl, substituted cycloalkyl, alkoxycarbonyl, carbonyloxy, alkoxy, aminocarbonyl, carbonylamino, dialkylamino, silyl groups or derivatives thereof, and alkyl or aryl groups substituted with any of these substituents or halogen or a nitro group. More preferably $R^{5'}$ is an alkyl, substituted alkyl (including heterocyclic substituted alkyl with at one heteroatom, such as N or O, and alkyl groups substituted with a heteroatom or heteroatomic group), cycloalkyl, substituted cycloalkyl, substituted cyclic aryl, substituted aryl, aryloxy or substituted aryloxy group. Examples of suitable $R^{5'}$ groups include $C_1$-$C_{15}$ alkyl groups, substituted $C_1$-$C_{15}$ alkyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups. Most preferred $R^{5'}$ groups are the $C_1$-$C_{15}$ alkyl groups, which include both linear and branched alkyl groups, suitable examples include methyl, ethyl, propyl, isopropyl, butyl, isobutyl, t-butyl, pentyl, alkyl branched pentyl groups, hexyl, alkyl branched hexyl groups, heptyl, alkyl branched heptyl groups, octyl and alkyl branched octyl groups.

Examples of suitable bridging groups may include —N(methyl)-, —N(ethyl)-, —N(propyl)-, —N(isopropyl)-, —N(butyl)-, —N(t-butyl)-, —N(pentyl)-, —N(hexyl)-, —N(2-ethylhexyl)-, —N(cyclohexyl)-, —N(1-cyclohexylethyl)-, —N(2-methylcyclohexyl)-, —N(benzyl)-, —N(phenyl)-, —N(2-octyl)-, —N(p-methoxyphenyl)-, —N(p-t-butylphenyl)-, —N(($CH_2$)$_3$—N—morpholine)-, —N(Si($CH_3$)$_3$)—, —N($CH_2CH_2CH_2$Si(OMe)$_3$))—, —N(decyl)- and —N(allyl)-.

The $R^{1'}$, $R^{2'}$, $R^{3'}$ and $R^{4'}$ groups of the second ligand may be independently selected from hydrocarbyl, substituted hydrocarbyl, heterohydrocarbyl and substituted heterohydrocarbyl groups. In one embodiment, the $R^{1'}$, $R^{2'}$, $R^{3'}$ and $R^{4'}$ groups of the second ligand may be independently selected from aromatic and substituted aromatic groups, including heteroaromatic and substituted heteroaromatic groups. Suitable $R^{1'}$, $R^{2'}$, $R^{3'}$ and $R^{4'}$ groups may be independently selected from a group comprising optionally substituted benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl groups. Preferably, $R^{1'}$, $R^{2'}$, $R^{3'}$ and $R^{4'}$ may be independently selected from a group comprising optionally substituted phenyl, tolyl, biphenyl, naphthyl, thiophenyl and ethyl groups.

Any of the groups $R^{1'}$, $R^{2'}$, $R^{3'}$ and $R^{4'}$ may independently be linked to one or more of each other or to the bridging group X' to form a cyclic structure.

In the first embodiment of the second ligand wherein at least one of $R^{1'}$, $R^{2'}$, $R^{3'}$ and $R^{4'}$ may be substituted with a polar substituent, up to four of $R^{1'}$, $R^{2'}$, $R^{3'}$ and $R^{4'}$ may have a substituents on an atom adjacent to the atom bound to the phosphorus atom.

In addition to at least one of $R^{1'}$, $R^{2'}$, $R^{3'}$ and $R^{4'}$ being substituted with a polar substituent, each of $R^{1'}$, $R^{2'}$, $R^{3'}$ and $R^{4'}$ may be aromatic, including heteroaromatic, but preferably not all of $R^{1'}$, $R^{2'}$, $R^{3'}$ and $R^{4'}$, if they are all aromatic, are substituted by any substituent on an atom adjacent to the atom bound to the phosphorus atom; preferably not more than two of $R^{1'}$, $R^{2'}$, $R^{3'}$ and $R^{4'}$, if they are aromatic, may have substituents on the atom adjacent to the atom bound to the phosphorus atom.

Any polar substituents on $R^{1'}$, $R^{2'}$, $R^{3'}$ and $R^{4'}$, if they are aromatic, may preferably not be on the atom adjacent to the atom bound to the phosphorus atom.

At least one of $R^{1'}$, $R^{2'}$, $R^{3'}$ and $R^{4'}$, if aromatic, may be substituted with a polar substituent on the second or further atom from the atom bound to the phosphorus atom.

Any polar substituent on one or more of $R^{1'}$, $R^{2'}$, $R^{3'}$ and $R^{4'}$ may be electron donating.

Suitable polar substituents may include methoxy, ethoxy, isopropoxy, $C_3$-$C_{20}$ alkoxy, phenoxy, pentafluorophenoxy, trimethylsiloxy, dimethylamino, methylsulfonyl, tosyl, methoxymethyl, methylthiomethyl, 1,3-oxazolyl, methomethoxy, hydroxyl, amino, phosphino, arsino, stibino, sulphate, nitro and the like.

In the second embodiment of the second ligand wherein $R^{1'}$, $R^{2'}$, $R^{3'}$ and $R^{4'}$ may be independently selected from hydrocarbyl, substituted hydrocarbyl, heterohydrocarbyl and substituted heterohydrocarbyl groups, wherein any substituents on one or more of $R^{1'}$, $R^{2'}$, $R^{3'}$ and $R^{4'}$ may be non-polar, preferably the $R^{1'}$, $R^{2'}$, $R^{3'}$ and $R^{4'}$ groups may be independently optionally substituted non-aromatic ring or aromatic, including heteroaromatic, groups. In addition, not all the groups $R^{1'}$, $R^{2'}$, $R^{3'}$ and $R^{4'}$, if aromatic, have a non-polar substituent on the atom adjacent to the atom bound to the phosphorus atom.

Any substituents on one or more of $R^{1'}$, $R^{2'}$, $R^{3'}$ and $R^{4'}$ may not be electron donating.

IUPAC defines non-polar as an entity without a permanent electric dipole moment.

Suitable non-polar substituents may be a methyl, ethyl, propyl, butyl, isopropyl, isobutyl, tert-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, propenyl and benzyl group, or the like.

In one embodiment of the second embodiment of the second ligand, $R^{1'}$, $R^{2'}$, $R^{3'}$ and $R^{4'}$ may be unsubstituted non-aromatic ring or aromatic, including heteroaromatic, groups.

In another embodiment of the present invention, one or both of the phosphorus atoms of the second ligand may be independently oxidised by S, Se, N or O.

The ligand may also contain multiple $(R^{1'})(R^{2'})P$—X'—$P(R^{3'})(R^{4'})$ units. Non limiting examples of such ligands include ligands where the individual units are coupled either via one or more of the $R^{1'}$, $R^{2'}$, $R^{3'}$ or $R^{4'}$ groups or via the bridging group X'.

The ligands may be prepared using procedures known to one skilled in the art and procedures disclosed in published literature.

Examples of the ligands wherein $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups of which at least one of $R^{1'}$, $R^{2'}$, $R^{3'}$ and $R^{4'}$ is substituted with a polar substituent include: (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4-methoxyphenyl)$_2$, (3-methoxyphenyl)(phenyl) PN(methyl)P(phenyl)$_2$, (4-methoxyphenyl)(phenyl) PN(methyl)P(phenyl)$_2$, (3-methoxyphenyl)(phenyl) PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)$_2$, (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN(2-methylcyclohexyl)P(4-methoxyphenyl)$_2$, (4-methoxyphenyl)$_2$PN(decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (4-fluorophenyl)$_2$PN(methyl)P(4-fluorophenyl)$_2$, (2-fluorophenyl)$_2$PN(methyl)P(2-fluorophenyl)$_2$, (4-dimethylamino-phenyl)2PN(methyl)P(4-dimethylamino-phenyl)$_2$, (4-methoxyphenyl)$_2$PN(allyl)P(4-methoxyphenyl)$_2$, (phenyl)$_2$PN(isopropyl)P(2-methoxyphenyl)$_2$, (4-(4-methoxyphenyl)-phenyl)$_2$PN(isopropyl)P(4-(4-methoxyphenyl)-phenyl)$_2$, (4-methoxyphenyl)(phenyl)PN(isopropyl)P (phenyl)$_2$, 1,2-di-(N(P(4-methoxyphenyl)$_2$)$_2$)-benzene, 1,4-di-(N(P(4-methoxyphenyl)2)2)-benzene, N(CH$_2$CH$_2$N(P(4-methoxyphenyl)$_2$)$_2$)$_3$ and 1,4-di-(P(4-methoxyphenyl)N(methyl)P(4-methoxyphenyl)2)-benzene. Preferred ligands from the above list include: (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (3-methoxyphenyl)$_2$PN(methyl)P(phenyl)$_2$, (4-methoxyphenyl)$_2$PN(methyl)P(phenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, and (phenyl)$_2$PN(isopropyl)P(2-methoxyphenyl)$_2$.

Examples of the ligands wherein $R^{1'}$, $R^{2'}$, $R^{3'}$ and $R^{4'}$ are independently selected from hydrocarbyl, substituted hydrocarbyl, heterohydrocarbyl and substituted heterohydrocarbyl groups, wherein any substituents on one or more of $R^{1'}$, $R^{2'}$, $R^{3'}$ and $R^{4'}$ are non-polar include: (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-t-butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (ethyl)$_2$PN(methyl)P(ethyl)$_2$, (ethyl)$_2$PN(isopropyl)P(phenyl)$_2$, (ethyl)(phenyl)PN(methyl)P(ethyl)(phenyl), (ethyl)(phenyl)PN(isopropyl)P(phenyl)$_2$, (phenyl)$_2$P(=Se)N(isopropyl)P(phenyl)$_2$, (o-ethylphenyl)(phenyl)PN(isopropyl)P(phenyl)$_2$, (o-methylphenyl)$_2$PN(isopropyl)P(o-methylphenyl)(phenyl), (phenyl)$_2$PN(benzyl)P(phenyl)$_2$, (phenyl)$_2$PN(1-cyclohexyl-ethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, (phenyl)$_2$PN(2-methylcyclohexyl)P(phenyl)$_2$, (phenyl)$_2$PN(allyl)P(phenyl)$_2$, (2-naphthyl)$_2$PN(methyl)P(2-naphthyl)$_2$, (p-biphenyl)$_2$PN(methyl)P(p-biphenyl)$_2$, (p-methylphenyl)$_2$PN(methyl)P(p-methylphenyl)$_2$, (2-thiophenyl)$_2$PN(methyl)P(2-thiophenyl)$_2$, (m-methylphenyl)$_2$PN(methyl)P(m-methylphenyl)$_2$, (phenyl)$_2$PN(isopropyl)P(phenyl)$_2$, (phenyl)$_2$P(=S)N(isopropyl)P(phenyl)$_2$, 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$ and 1,4-di-(P(phenyl)N(methyl)P(phenyl)$_2$)-benzene.

The catalyst precursor composition and catalyst system of the present invention may independently comprise more than one first ligand as defined above and more than one second ligand as defined above.

The first ligand and the second ligand may be present in the catalyst system in a molar ratio in the range of from 100:1 to 1:100. In a preferred embodiment the molar ratio of the first ligand to the second ligand is in the range of from about 10:1 to about 1:10, more preferably in the range of from about 5:1 to about 1:5.

By varying the ratio of the first ligand and the second ligand in the catalyst precursor composition or the catalyst system of the present invention, the ratio of trimers and tetramers produced in the process of the present invention may be varied. As a general principle, by increasing the amount of the first ligand relative to the second ligand in the catalyst system, the concentration of trimers in the reaction product composition increases relative to the concentration of the tetramers in the reaction product composition, and vice-versa.

Therefore, the catalyst system of the present invention may be used in a tuneable process for the trimerization and tetramerization of olefinic monomers. By the term "tuneable" as used herein, it is meant that by varying the amounts of the components of the present invention, the amount of trimers and tetramers in the product composition produced by the process of the present invention may be varied. This may be useful for a tuneable, continuous or semi-continuous, process for the trimerization and tetramerization of olefinic monomers, wherein the product composition may be changed (e.g. from producing a higher proportion of trimers to a higher proportion of tetramers, or vice-versa,) by changing the ratio of the first and second ligand that are fed into the reactor without having to interrupt the olefinic monomer feed or the trimerization and tetramerization product flow. In particular, this may be especially useful for a tuneable, continuous or semi-continuous, process for the trimerization and tetramerization of ethylene, wherein the product composition may be changed (e.g. from producing a higher proportion of 1-hexene to a higher proportion of 1-octene, or vice-versa) by changing the ratio of the first and second ligand that are fed into the reactor without having to interrupt the olefinic monomer feed or the trimerization and tetramerization product flow.

The amount of chromium, molybdenum or tungsten, namely component (a), and the total amount of the ligand components, i.e. the combined amount of the first and second ligands, namely components (b) and (c), which may be present in the catalyst precursor composition or the catalyst system of the present invention may be present in a molar ratio in the range from 10000:1 to 1:10000, preferably from 100:1 to 1:100, more preferably from 10:1 to 1:10. Most preferably, the chromium, molybdenum or tungsten, component (a), and the combined amounts of the ligand components, components (b) and (c), may be present in a molar ratio in the range from 3:1 to 1:3. Generally the amounts of component (a) and the combined amount of components (b) and (c) may be approximately equal, i.e. a molar ratio in the range from 1.5:1 to 1:1.5.

The cocatalyst, component (d), may in principle be any compound or mixture of compounds that generates an active catalyst system with the source of chromium, molybdenum or tungsten, component (a), and the first and second ligands, components (b) and (c) (i.e. the catalyst precursor composition).

Compounds which may be suitable for use as a cocatalyst include organoaluminium compounds, organoboron compounds, organic salts, such as methyllithium and methylmagnesium bromide and inorganic acids and salts, such as tetrafluoroboric acid etherate, silver tetrafluoroborate, sodium hexafluoroantimonate and the like.

Particularly preferred cocatalysts may be organoaluminium compounds. Suitable organoaluminium compounds for use herein may be those having the formula AlR$^6$$_3$, wherein each $R^6$ group is independently selected from C$_1$-C$_{30}$ alkyl (preferably C$_1$-C$_{12}$ alkyl), oxygen containing moieties or halides, and compounds such as LiAlH$_4$ and the like. Non-limiting examples of suitable organoaluminium compounds may include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride and aluminoxanes (also called alumoxanes). Mixtures of organoaluminium compounds may also suitable for use herein.

In a preferred embodiment herein, the cocatalyst may be an aluminoxane cocatalyst. These aluminoxane cocatalysts may comprise any aluminoxane compound or a mixture of aluminoxane compounds. Aluminoxanes may be prepared by the controlled addition of water to an alkylaluminium compound, such as those mentioned above, or are available commercially. In this context it should be noted that the term "aluminoxane" as used within this specification includes commercially available aluminoxanes, which are derived from the corresponding trialkylaluminium by addition of water and which may contain typically about 5% wt., but optionally about 10% wt., of aluminium.

Other suitable co-catalysts may include those disclosed in U.S. Pat. No. 6,800,702, WO 2004/056478 and WO 2004/056479, which are incorporated herein in their entirety by reference.

The quantity of cocatalyst in the catalyst system the present invention may be typically enough to provide a ratio in the range from 0.1 to 20,000, preferably from 1 to 2000, more preferably 1 to 1000, most preferably 1 to 500, aluminium or boron atoms per atom of chromium, molybdenum or tungsten.

The three components of the catalyst precursor composition, (a), (b) and (c), and the fourth component of the catalyst system, (d), may be added together simultaneously or sequentially in any order so as to provide an active catalyst. The three components of the catalyst precursor composition, (a), (b) and (c), and the fourth component of the catalyst system, (d), may be contacted in the presence of any suitable solvent. Suitable solvents are known to those skilled in the art. Suitable solvents may include any inert solvent that does not react with the co-catalyst component, such as saturated aliphatic, unsaturated aliphatic, aromatic, halogenated hydrocarbons and ionic liquids. Typical solvents may include, but are not limited to, benzene, toluene, xylene, ethylbenzene, cumene, propane, butane, pentane, heptane, decane, dodecane, tetradecane, methylcyclohexane, methylcycopentane, cyclohexane, 1-hexene, 1-octene and the like. Other examples of suitable solvents are those disclosed in WO 02/04119, such as hydrocarbon solvents and polar solvents such as diethyl ether, tetrahydrofuran, acetonitrile, dichloromethane, chloroform, chlorobenzene and the like. If MAO is used as the cocatalyst component, (d), the solvent is preferably not a chlorinated solvent.

In one embodiment of the present invention, the catalyst system may be formed by adding the co-catalyst component, (d), to a catalyst precursor composition of the present invention.

The catalyst system of the present invention may be prepared either in the presence (i.e. "in-situ") or absence of the olefinic monomer. The three components of the catalyst precursor composition, (a), (b) and (c) and the fourth component of the catalyst system, (d), may be combined fully in the absence of the olefinic monomer, or the olefinic monomer may be included prior to contacting the components of the catalyst system, simultaneously with the components of the catalyst system or at any point in the process of contacting the components of the catalyst.

Another method for forming the catalyst system of the present invention may include combining a first solution of components (a) and (b), and optionally component (d), with a second solution of components (a) and (c), and optionally component (d), wherein additional amounts of components (a), (b), (c) and (d) may be further added to the combined solution, if necessary, to form the desired catalyst system. The combining of the above mentioned first and second solutions and any additional components may be performed either in-situ or in the absence of the olefinic monomer.

The three components of the catalyst precursor composition, (a), (b) and (c), and the fourth component of the catalyst system, (d), may be combined at a temperature in the range of from −100 to 200° C., preferably 0 to 150° C., more preferably 20 to 100° C.

The catalyst system of the present invention may be unsupported or supported on a support material. Examples of suitable support materials can be found in U.S. Pat. No. 6,800,702, WO 2004/056478 and WO 2004/056479, which are herein incorporated by reference.

The olefinic monomers suitable for use in the trimerization and tetramerization process of the present invention may be any olefinic monomers which may be converted into a trimer or tetramer. Suitable olefinic monomers may include, but are not necessarily limited to, ethylene, propylene, optionally branched $C_4$-$C_{20}$ α-olefins, optionally branched $C_4$-$C_{20}$ internal olefins, optionally branched $C_4$-$C_{20}$ vinylidene olefins, optionally branched $C_4$-$C_{20}$ cyclic olefins and optionally branched $C_4$-$C_{20}$ dienes, as well as optionally branched $C_4$-$C_{20}$ functionalized olefins. Examples of suitable olefinic monomers may include, but are not necessarily limited to, linear α-olefins, such as ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene and 1-eicosene; branched a-olefins such as 4-methylpent-1-ene and 1-ethyl-1-hexene; linear and branched internal-olefins such as 2-butene; styrene; cyclohexene; norbornene and the like.

Mixtures of olefinic monomers may also be used in the process of the present invention.

Preferred olefinic monomers for use in the trimerization and tetramerization process of the present invention are propylene and ethylene. Especially preferred is ethylene.

The catalyst system and process of the present invention are particularly useful for the simultaneous trimerization and tetramerization of ethylene to 1-hexene and 1-octene.

The trimerization and tetramerization process of the present invention may be performed under a range of process conditions known to one skilled in the art or disclosed in published literature such as, for example, those disclosed in U.S. Pat. No. 6,800,702, WO2004/056478 and WO2004/056479, which are herein incorporated by reference.

The simultaneous trimerization and tetramerization reaction may be performed in solution phase, slurry phase, gas phase or bulk phase.

When the simultaneous trimerization and tetramerization may be performed in solution or slurry phase, a diluent or solvent, which is substantially inert under trimerization and tetramerization conditions may be employed. Suitable diluents or solvents may be aliphatic and aromatic hydrocarbons, halogenated hydrocarbons and olefins which are substantially inert under trimerization and tetramerization conditions may be employed, such as those disclosed in U.S. Pat. No. 6,800,702, WO2004/056478 and WO2004/056479, which are herein incorporated by reference.

The trimerization and tetramerization process of the present invention may be performed in any one of a number of suitable reactors, which are well known to one skilled in the art. Typically the trimerization and tetramerization process of the present invention may be carried out in a batch, semi-batch or continuous mode.

The trimerization and tetramerization process of the present invention may be carried out under a wide range of reaction conditions, which are well known to a person skilled in the art. Typically, the temperature may be in the range from −100° C. to 200° C., preferably from 0° C. to 150° C., and more preferably from 20° C. to 100° C. The pressure range under which the process of the present invention may be performed is not critical and may vary depending upon the limitations of the reactor. Typically the reaction pressure may be in the range of from below atmospheric pressure to about 500 barg. Preferably, the pressure may be in the range from 0 to 100 barg, more preferably from 1 to 50 barg.

In one embodiment of the present invention, there is a process for the trimerization and tetramerization of olefinic monomers, wherein the process comprises contacting at least one olefinic monomer under trimerization and tetramerization reaction conditions with a catalyst system of the present invention, wherein the process may be a continuous or semi-continuous process and the ratio of the catalyst components, especially the ratio of the first ligand and the second ligand, may be varied during the process. A preferred version of this embodiment is a process for the trimerization and tetramerization of ethylene, wherein the process comprises contacting ethylene under trimerization and tetramerization reaction conditions with a catalyst system of the present invention, wherein the process is a continuous or semi-continuous process and the ratio of the catalyst components, especially the first ligand and the second ligand, may be varied during the process.

Separation of the products, reactant and catalyst may be performed by any technique known to one skilled in the art, such as distillation, filtration, centrifugation, liquid/liquid separation, extraction, etc.

Further details regarding suitable reaction conditions, including further details on reactors, solvents, separation techniques, and the like, may be found in U.S. Pat. No. 6,800,702, which is herein incorporated by reference.

The use of the catalyst system and process of the present invention for the catalytic trimerization and tetramerization of olefinic monomers provides a simplified method of producing trimers and tetramers of the olefinic monomer with reduced formation of by-products compared with the combination of the product compositions of separate trimerization and tetramerization processes. In particular, the use of the catalyst system and process of the present invention for the catalytic trimerization and tetramerization of ethylene to 1-hexene and 1-octene provides a process with very high selectivity for 1-hexene and 1-octene over all the other products formed in the reaction.

The overall yield of 1-hexene and 1-octene in the process of the present invention depends upon the ratio of the first ligand, component (b), and the second ligand, component (c).

The trimerization and tetramerization selectivity (i.e. the amount of trimers and tetramers of the olefinic monomers in the overall product composition) of the process of the present invention may be at least 70% wt (percent by weight), preferably at least 80% wt, more preferably at least 90% wt, of the overall product composition. The trimerization and tetramerization selectivity (i.e. the amount of $C_6$ and $C_8$ fraction in the overall product composition) for the trimerization and tetramerization of ethylene using the catalyst system of the present invention may be at least 80% wt, preferably at least 85% wt, more preferably at least 90% wt, of the overall product composition.

The amount of 1-hexene produced by the trimerization and tetramerization of ethylene using the catalyst system of the present invention may be typically in the range of from 15% wt to 85% wt, preferably from 20% wt to 80% wt, more preferably from 25% wt to 75% wt, of the overall product composition. The amount of 1-octene produced by the trimerization and tetramerization of ethylene using the catalyst system of the present invention may be typically in the range of from 15% wt to 85% wt, preferably from 20% wt to 80% wt, more preferably from 25% wt to 75% wt, of the overall product composition.

The 1-hexene selectivity (i.e. the amount of 1-hexene present in the $C_6$ fraction of the product composition) in the trimerization and tetramerization of ethylene using the catalyst system of the present invention is preferably at least 75% wt, more preferably at least 80% wt, even more preferably at least 85% wt and most preferably at least 90% wt, of the $C_6$ fraction of the product composition.

The 1-octene selectivity (i.e. the amount of 1-octene present in the $C_8$ fraction of the product composition) in the trimerization and tetramerization of ethylene using the catalyst system of the present invention is preferably at least 75% wt, more preferably at least 80% wt, even more preferably at least 85% wt and most preferably at least 90% wt, $C_8$ fraction of the product composition.

In practice, the combined 1-hexene selectivity and the 1-octene selectivity is typically at least 88% wt of the overall product composition.

In another embodiment of the present invention, the olefinic product composition of the trimerization and tetramerization of ethylene using the catalyst system of the present invention typically may comprise a combined total content of 1-hexene and 1-octene in the range of from 88 to 98% wt of the overall product composition, preferably from 90 to 98% wt and more preferably from 92 to 98% wt, wherein the 1-hexene content may be at least 15% wt, more preferably at least 20% wt and most preferably at least 25% wt, of the overall product composition and the 1-octene content is at least 15% wt, more preferably at least 20% wt and most preferably at least 25% wt, of the overall product composition.

In further embodiment of the present invention, the olefinic product composition of the trimerization and tetramerization of ethylene using the catalyst system of the present invention may comprise a total content of compounds other than 1-hexene and 1-octene of at most 12% wt of the overall product composition, preferably at most 10% wt and more preferably at most 8% wt, wherein the 1-hexene content may be at least 15% wt, more preferably at least 20% wt and most preferably at least 25% wt, of the overall product composition and the 1-octene content may be at least 15% wt, more preferably at least 20% wt and most preferably at least 25% wt, of the overall product composition. Typically, the olefinic product composition of the trimerization and tetramerization of ethylene using the catalyst system of the present invention may comprise a total content of compounds other than 1-hexene and 1-octene in the range of from 2 to 12 % wt of the overall product composition, preferably from 2 to 10% wt and more preferably from 2 to 8% wt, wherein the 1-hexene content may be at least 25% wt of the overall product composition and the 1-octene content may be at least 25% wt of the overall product composition. Typically, the product composition may also comprise at least 0.25% wt of $C_6$ compounds other than 1-hexene, at least 0.25% wt of $C_8$ compounds other than 1-octene, at least 0.5% wt of $C_{10}$ compounds and at least 0.5% wt of hydrocarbon compounds comprising 12 or more carbon atoms.

The catalyst systems and process of the present invention are illustrated by the following non-limiting examples.

EXAMPLES

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures. Anhydrous toluene (99.8% purity) was dried over 4 Å molecular sieves (final water content of about 3 ppm). Anhydrous heptane (99.8% purity) was dried by passage over 4 Å molecular sieves (final water content of about 1 ppm).

Ethylene (99.5% purity) was purified over a column containing 4 Å molecular sieves and BTS catalyst (BASF) in order to reduce water and oxygen content to <1 ppm.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 µm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. The yields of the $C_4$-$C_{30}$ olefins were obtained from the GC analysis.

The "trimerization selectivity", "tetramerization selectivity", "1-hexene selectivity" and "1-octene selectivity" were all determined by GC analysis.

The amount of "solids", mainly consisting of heavy wax and polyethylene, has been determined by weighing, after its isolation from the reactor wall and appendages, followed by washing with toluene on a glass filter (P3) and by vacuum drying.

The amount of "total product" is the sum of the amount of largely olefinic product derived from GC analysis and the amount of solids.

The NMR data was obtained at room temperature with a Varian 300 MHz or 400 MHz apparatus.

Catalyst Systems

The catalyst systems of the present invention were prepared from catalyst precursor compositions containing ligands A and/or B and a chromium source, these components are described below.

Chromium Source

Chromium tris-(2,4-pentanedionate), also called chromium tris(acetylacetonate), has been used as the chromium source in the simultaneous trimerization and tetramerization reactions of ethylene.

Ligand A (First Ligand)

The (2-methoxyphenyl)(phenyl)PCH$_2$CH$_2$P(2-methoxyphenyl)(phenyl) ligand is prepared according to the following method.

Under a nitrogen atmosphere, to a solution of o-bromoanisole (0.54 mol) in pentane (150 ml), n-butyllithium solution (337 ml, 0.54 mol) is added slowly with constant stirring. The mixture is stirred overnight, after which, the stirring is stopped and the suspension is allowed to settle out. The liquor is decanted and the solid residue of o-anisyllithium is washed with pentane and dried under high vacuum.

0.20 mol of o-anisyllithium is dissolved in diethyl ether (400 ml) and cooled to −20° C. Slowly added under constant stirring to this solution is 0.1 mol ethyl phenylphosphinate. The solution is then allowed to reach 25° C., after which the solution is then refluxed for 2 hours. The solution is then allowed to cool, after which 0.1 M hydrochloric acid is added (150 ml). The product is then extracted with three 50 ml portions of dichloromethane. The combined organic layers are then combined and dried using magnesium sulfate. The solvents are then removed to give an oil and then excess anisole is removed by warming (70° C.) under vacuum. The last traces of anisole are removed by washing the resultant white solid ((2-methoxyphenyl)(phenyl) phosphine oxide) with diethyl ether, followed by crystallisation from chloroform/diethyl ether.

40 mmol of the (2-methoxyphenyl)(phenyl)phosphine oxide is added to tetrahydrofuran (600 ml), to which n-butyllithium solution (25 ml, 40 mmol) is added at 0° C. The orange homogeneous solution of the lithium salt formed is then allowed to stir for 1 hour at room temperature and then cooled to 0° C. To this solution 1,2-ethanediyl bis-tosylate (20 mmol) is added. The temperature of the solution is then allowed to increase to room temperature. A slurry is formed as the solution is heated and refluxed overnight. The mixture is then cooled and the reaction is quenched by the addition of water (150 ml). The product is then extracted into dichloromethane (3×100 ml) followed by drying with magnesium sulfate. Concentration of the solution affords the 1,2-ethandiyl(2-methoxyphenyl)(phenyl)phosphine oxide product as a white solid.

To a 2 mmol solution of the 1,2-ethandiyl(2-methoxyphenyl)(phenyl)phosphine oxide product in tetrahydrofuran (250 ml), aluminium hydride (AlH$_3$.1/3(C$_2$H$_5$)$_2$O, 20-mmol) is added dropwise. The solution is then refluxed until complete (generally overnight), after which, the reaction is quenched by the addition of methanol (10 ml), followed by the filtration of the aluminium salt precipitate. The filtrate is then concentrated. Addition of methanol affords the crystalline (2-methoxyphenyl)(phenyl) PCH$_2$CH$_2$P(2-methoxyphenyl)(phenyl) product.

Ligand B (Second Ligand)

The (phenyl)$_2$PN(isopropyl)P(phenyl)$_2$ ligand was prepared by the following method. At 0° C., under a nitrogen atmosphere, 15 ml triethylamine was added to 6.3 g (phenyl)$_2$ PCl in 80 ml of dry dichloromethane. To the resulting mixture, 0.844 g isopropylamine was added and allowed to stir overnight at room temperature. The solvents were removed from the resulting solution in-vacuo and 50 ml of dry toluene was added. The mixture was then filtered over a small layer of silica. The toluene was removed from the filtrate under vacuum, (phenyl)$_2$PN(isopropyl)P(phenyl)$_2$ product was isolated as a white solid. Crystallization from ethanol yields (phenyl)$_2$PN(isopropyl)P(phenyl)$_2$ as white crystals.

Co-Catalyst

The co-catalyst used in the experiments below was selected from:

modified methyl aluminoxane (MMAO) wherein about 25% of the methyl groups are replaced with isobutyl groups. MMAO-3A in heptane ([Al]=6.42% wt), available from AKZO-NOBEL Chemicals B. V., Amersfoort, The Netherlands;

methyl aluminoxane (MAO) in toluene, [Al]=5.20% wt, supplied by Crompton GmbH, Bergkamen, Germany.

Examples 1-5

Catalyst System Preparation for Simultaneous Trimerization and Tetramerization in a Batch Autoclave In a Braun MB 200-G dry box the chromium tris(acetylacetonate) (typically 30 μmol) and the amounts of ligand components, indicated in Table 1, were placed in a glass bottle, to which dry toluene (typically 4 g) was added to obtain the catalyst precursor solution. Finally the bottle was sealed by a septum cap. These solutions or part of these solutions were used in the simultaneous trimerization and tetramerization reaction of ethylene.

Simultaneous Trimerization and Tetramerization Reactions of Ethylene in a 1.0-Liter Batch Autoclave Simultaneous trimerization and tetramerization experiments were performed in a 1.0-liter steel autoclave equipped with jacket cooling with a heating/cooling bath (ex. Julabo, model ATS-2) and a turbine/gas stirrer and baffles.

The reactor was scavenged by introducing 250 ml of toluene and 0.6 g of the MAO solution and subsequent stirring at 70° C. under nitrogen pressure of 0.4-0.5 MPa for 30 min. The reactor contents were discharged via a tap in the base of the autoclave. The reactor was evacuated to about 0.4 kPa and loaded with approximately 250 ml toluene or heptane, heated to 40° C. and pressurised with ethylene to 15 barg.

Whilst stirring, a MAO-solution (typically an intake of 3.12 g, 6 mmol Al, to attain an Al/Cr atomic ratio of 200) was added to the reactor with the aid of toluene (the total volume injected was about 25 ml: the MAO-solution diluted with toluene to 8 ml was injected and the injector system was rinsed twice with 8 ml toluene) and the stirring at 800 rpm was continued for 30 minutes.

The Cr-catalyst system (typically 30 μmol on Cr intake) prepared as described above was introduced into the stirred reactor using an injection system with the aid of toluene (the total volume injected was about 25 ml: the catalyst solution diluted with toluene to 8 ml was injected and the injector system was rinsed twice with 8 ml toluene). The initial loading of the reactor was about 300 ml of largely toluene.

The addition of the catalyst system resulted, after an induction period of some 5 minutes, in an exotherm (generally some 5-10° C.), which generally reached a maximum within 1 minute and was followed by establishment of the temperature of 40° C. and the pressure of 15 barg.

After consuming the desired volume of ethylene, the simultaneous tri- and tetramerization was stopped by rapid cooling to room temperature (in about 5 minutes), followed by venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product, the amount of the $C_4$-$C_{30}$ olefins and purity of $C_6$, $C_8$ and $C_{10}$ olefins was determined by gas chromatography. The experimental data is reported in Table 1.

In the case of experiments under 30 barg of ethylene pressure a similarly equipped 0.5-liter steel autoclave has been used, loaded (similarly to the above-described procedure for the 1.0-liter autoclave) with 150 ml of toluene, a MAO-solution and a Cr-catalyst system. The amounts of the Cr-catalyst system, MAO-solution, solvent and ethylene consumption were typically half of those used in the corresponding 1.0-liter experiments to maintain the same Al/Cr atomic ratio (of about 200) and final alpha olefin concentration as much as practicable.

The experimental data is provided in Table 1 below.

TABLE 1

| Example | Ligand(s) (A mol/B mol) / (Cr mol) | Time (min) | TON[†] | $C_6$ (% wt) | 1-$C_6$[‡] (% wt) | $C_8$ (% wt) | 1-$C_8$[*] (% wt) | $C_{10}$[**] (% wt) | $C_{12}$-$C_{14}$ (% wt) | Solids (g); (% wt) | Total Product (g) | 1-$C_6$ + 1-$C_8$ on Total (% wt) |
|---|---|---|---|---|---|---|---|---|---|---|---|---|
| 1 | A/B (0.9/0.3) / (1.0) | 130 | 20 | 62.7 | 95.9 | 30.0 | 99.2 | 1.4 | 1.3 | 0.2 (1.1) | 17.4 | 89.9 |
| 2[#] | A/B (0.9/0.3) / (1.0) | 71 | 47 | 41.8 | 91.4 | 49.8 | 98.3 | 1.7 | 1.9 | 0.25 (1.3) | 19.4 | 87.2 |
| 3 | A/B (0.7/0.6) / (1.0) | 130 | 26 | 48.6 | 91.9 | 45.1 | 99.1 | 1.5 | 2.1 | 0.2 (0.9) | 23.2 | 89.4 |
| 4[##] | B (1.1) / (1.0) | 120 | 32 | 22.4 | 79.4 | 69.2 | 99.1 | 1.4[†‡] | 3.6 | 0.3 (1.1) | 27.0 | 86.4 |

TABLE 1-continued

| Example | Ligand(s) (A mol/B mol) / (Cr mol) | Time (min) | TON† | C₆ (% wt) | 1-C₆‡ (% wt) | C₈ (% wt) | 1-C₈* (% wt) | C₁₀** (% wt) | C₁₂–C₁₄ (% wt) | Solids (g); (% wt) | Total Product (g) | 1-C₆ + 1-C₈ on Total (% wt) |
|---|---|---|---|---|---|---|---|---|---|---|---|---|
| 5#,## | B (1.1) (1.0) | 33.3 | 113 | 17.4 | 68.5 | 70.2 | 98.8 | 1.8†‡ | 4.4 | 0.2 (0.5) | 47.2 | 81.3 |

†Turn over number, TON in kmol converted ethylene/mol catalyst.
‡% of 1-hexene by weight of the C₆ portion of the product composition.
*% of 1-octene by weight of the C₈ portion of the product composition.
**Predominantly branched and/or internal decenes, unless indicated differently.
Carried out at 30 barg, instead of 15 barg.
Comparative example.
†‡About 50% of 1-decene by weight of the C₁₀ portion of the product composition.
C₆ Hydrocarbons containing 6 carbon atoms; 1-C₆ is 1-hexene.
C₈ Hydrocarbons containing 8 carbon atoms; 1-C₈ is 1-octene.
C₁₀ Hydrocarbons containing 10 carbon atoms.
C₁₂–C₁₄ Hydrocarbons containing 12 and/or 14 carbon atoms.
Solids: The amount of wax and polyethylene isolated by filtration.
Total Product: The amount of C₄–C₁₀₀ olefins, derived from GC analysis, including the amount of solids.

It is evident from the results in Table 1 that the use of a Cr[III] catalyst system according to the present invention containing a mixture of ligands A and B results in a product mixture comprising predominantly high purity 1-hexene and 1-octene (examples 1-3).

It is also evident that the 1-hexene content of the C₆-fraction produced when using a Cr[III] catalyst system according to the present invention containing a mixture of ligands A and B is higher than that obtained with the catalyst derived from ligand B only (examples 1-3 compared with examples 4 and 5).

It is also evident that the use of a Cr[III] catalyst system according to the present invention containing a mixture of ligands A and B results in a product mixture containing a lower amount of by-products (i.e. C₆'s other than 1-hexene, C₈'s other than 1-octene, C₁₀'s, C₁₂-C₁₄'s and solids) than that obtained with the catalyst derived from ligand B only (examples 1-3 compared with examples 4 and 5).

What is claimed is:

1. A catalyst precursor composition comprising:
   a) a source of chromium, molybdenum or tungsten;
   b) a first ligand having the general formula (I);

$$(R^1)(R^2)P\text{---}X\text{---}P(R^3)(R^4) \quad (I)$$

wherein:
   X is a bivalent alkylene bridging group;
   $R^1$ and $R^3$ are independently selected from aromatic groups which do not contain a polar substituent at any of the ortho-positions;
   $R^2$ and $R^4$ are independently selected from optionally substituted aromatic groups, each $R^2$ and $R^4$ bearing a polar substituent on at least one of the ortho-positions; and
   c) a second ligand having the general formula (II);

$$(R^{1'})(R^{2'})P\text{---}X'\text{---}P(R^{3'})(R^{4'}) \quad (II)$$

wherein:
   X' is a bridging group of the formula —N(R⁵')—, wherein $R^{5'}$ is selected from hydrogen, a hydrocarbyl group, a substituted hydrocarbyl group, a heterohydrocarbyl group, a substituted heterohydrocarbyl group, a silyl group or derivative thereof; and
   $R^{1'}$, $R^{2'}$, $R^{3'}$ and $R^{4'}$ are independently selected from aromatic and substituted aromatic groups, including heteroaromatic and substituted heteroaromatic groups, of which at least one of $R^{1'}$, $R^{2'}$, $R^{3'}$ and $R^{4'}$ contains a polar substitutent, or $R^{1'}$, $R^{2'}$, $R^{3'}$ and $R^{4'}$ are independently selected from aromatic and substituted aromatic groups, including heteroaromatic and substituted heteroaromatic groups, wherein any substituents on one or more of $R^{1'}$, $R^{2'}$, $R^{3'}$ and $R^{4'}$ are non-polar.

2. A catalyst system comprising the catalyst precursor composition of claim 1 and a cocatalyst.

3. The catalyst system of claim 2 wherein X is an alkylene group which contains from 2 to 6 carbon atoms in the bridge.

4. The catalyst system of claim 2 wherein X is —CH₂CH₂—.

5. The catalyst system of claim 2 wherein $R^1$ and $R^3$ are independently selected from optionally substituted phenyl groups which do not contain a polar substituent at any of the ortho-positions.

6. The catalyst system of claim 2 wherein $R^2$ and $R^4$ are independently selected from optionally substituted phenyl groups wherein the polar substituent is an optionally branched C₁-C₂₀ alkoxy group.

7. The catalyst system of claim 2 wherein $R^2$ and $R^4$ are 2-methoxyphenyl groups.

8. The catalyst system of claim 2 wherein $R^{5'}$ is selected from C₁-C₁₅ alkyl groups, substituted C₁-C₁₅ alkyl groups, C₁-C₁₅ cycloalkyl groups, substituted C₁-C₁₅ cycloalkyl groups, C₁-C₁₅ aromatic groups, substituted C₁-C₁₅ aromatic groups, C₁-C₁₅ alkoxy groups and substituted C₁-C₁₅ alkoxy groups.

9. The catalyst system of claim 2 wherein at least one of $R^{1'}$, $R^{2'}$, $R^{3'}$ and $R^{4'}$ is substituted with a polar substituent selected from methoxy, ethoxy, isopropoxy, C₃-C₂₀ alkoxy, phenoxy, pentafluorophenoxy, trimethylsiloxy, dimethylamino, methylsulfonyl, tosyl, methoxymethyl, methylthiomethyl, 1,3-oxazolyl, methomethoxy, hydroxyl, amino, phosphino, arsino, stibino, sulphate, and nitro.

10. The catalyst system of claim 2 wherein the cocatalyst, component (d), is selected from methylaluminoxane or modified methylaluminoxane.

11. The catalyst system of claim 2 wherein the source of chromium, molybdenum or tungsten, (a) is a source of chromium.

12. The catalyst system of claim 11 wherein the source of chromium is chromium tris-(2,4-pentanedionate), Cr(acac)₃.

* * * * *